United States Patent
Eaton et al.

(10) Patent No.: US 9,302,054 B2
(45) Date of Patent: Apr. 5, 2016

(54) INJECTION DEVICES

(75) Inventors: Mark Eaton, Oxfordshire (GB); Jeremy Marshall, Oxford (GB)

(73) Assignee: OWEN MUMFORD LIMITED, Oxfordshire (GB)

( * ) Notice: Subject to any disclaimer, the term of this patent is extended or adjusted under 35 U.S.C. 154(b) by 347 days.

(21) Appl. No.: 13/318,392

(22) PCT Filed: Apr. 30, 2010

(86) PCT No.: PCT/GB2010/050723
§ 371 (c)(1),
(2), (4) Date: Dec. 2, 2011

(87) PCT Pub. No.: WO2010/125400
PCT Pub. Date: Nov. 4, 2010

(65) Prior Publication Data
US 2012/0095408 A1    Apr. 19, 2012

Related U.S. Application Data

(60) Provisional application No. 61/174,642, filed on May 1, 2009.

(30) Foreign Application Priority Data

May 1, 2009    (GB) .................................. 0907534.2

(51) Int. Cl.
*A61M 5/20*    (2006.01)
*A61M 5/32*    (2006.01)
(Continued)

(52) U.S. Cl.
CPC ........... *A61M 5/3205* (2013.01); *A61M 5/2033* (2013.01); *A61M 5/24* (2013.01);
(Continued)

(58) Field of Classification Search
CPC ............ A61M 5/3204; A61M 5/3205; A61M 2005/3254; A61M 5/3271; A61M 5/3272; A61M 5/3269
USPC ......................................... 604/198, 218, 220
See application file for complete search history.

(56) References Cited

U.S. PATENT DOCUMENTS 2,895,474 A    7/1959    Reznek
5,030,209 A  *  7/1991    Wanderer ............. A61B 5/1444
                                                                    604/198
(Continued)

FOREIGN PATENT DOCUMENTS

CH    GB 2438590 A  * 12/2007  .......... A61M 5/2033
EP    0824923        2/1998
(Continued)

OTHER PUBLICATIONS

International Search Report dated Dec. 1, 2010, corresponding to PCT/GB2010/050723.
(Continued)

*Primary Examiner* — Emily Schmidt
*Assistant Examiner* — William Frehe
(74) *Attorney, Agent, or Firm* — Young & Thompson

(57) ABSTRACT

An injection device includes a multi-use drive assembly 10 and a single use disposable syringe assembly 12 releasably connected thereto. The syringe assembly includes a syringe 18 and a shield 26 mounted for telescopic movement. The drive assembly 10 is operable to extend the syringe 18 relative to the shield 26 and then to express a dose. Continued forward drive movement extends the shield 26 to re-cover the syringe needle 22 and then ejects the spent syringe assembly 12 in a safe (shrouded) condition.

15 Claims, 5 Drawing Sheets

(51) Int. Cl.
*A61M 5/315* (2006.01)
*A61M 5/24* (2006.01)

(52) U.S. Cl.
CPC ............ *A61M 5/326* (2013.01); *A61M 5/3272* (2013.01); *A61M 5/31513* (2013.01); *A61M 5/31571* (2013.01); *A61M 5/3204* (2013.01); *A61M 2005/206* (2013.01); *A61M 2005/2073* (2013.01); *A61M 2005/2492* (2013.01); *A61M 2005/3151* (2013.01); *A61M 2005/31508* (2013.01); *A61M 2005/3254* (2013.01)

(56) References Cited

U.S. PATENT DOCUMENTS

| | | | | |
|---|---|---|---|---|
| 5,059,185 | A | * | 10/1991 | Ryan .................. A61M 5/3243 600/576 |
| 5,088,985 | A | * | 2/1992 | Deras ................. A61M 5/3243 128/919 |
| 5,295,965 | A | * | 3/1994 | Wilmot ............... A61M 5/2033 604/136 |
| 5,620,421 | A | | 4/1997 | Schmitz |
| 5,709,662 | A | * | 1/1998 | Olive ................. A61M 5/2033 604/110 |
| 5,843,036 | A | | 12/1998 | Olive et al. |
| 6,585,702 | B1 | * | 7/2003 | Brunel .......................... 604/263 |
| 6,899,698 | B2 | * | 5/2005 | Sams ........................... 604/211 |
| 2001/0005781 | A1 | | 6/2001 | Bergens et al. |
| 2006/0036217 | A1 | * | 2/2006 | Doyle ......................... 604/198 |
| 2006/0153693 | A1 | | 7/2006 | Fiechter et al. |
| 2007/0129686 | A1 | * | 6/2007 | Daily ................. A61M 5/2033 604/192 |
| 2007/0162063 | A1 | * | 7/2007 | Marshall et al. ............. 606/181 |
| 2008/0051715 | A1 | | 2/2008 | Young |
| 2008/0147006 | A1 | | 6/2008 | Brunnberg et al. |
| 2010/0204658 | A1 | | 8/2010 | Imai |
| 2011/0172602 | A1 | | 7/2011 | Eaton |

FOREIGN PATENT DOCUMENTS

| | | | |
|---|---|---|---|
| EP | 2 165 723 | | 3/2010 |
| FR | 2 342 079 | | 9/1977 |
| GB | 2438590 | * | 5/2007 .................... 604/134 |
| GB | 2438590 A | * | 12/2007 |
| GB | 2 463 071 | | 3/2010 |
| JP | 8 182760 | | 7/1996 |
| JP | 10-113388 | | 5/1998 |
| JP | 2003-220142 | | 8/2003 |
| WO | 00/24441 | | 5/2000 |
| WO | 2005/009515 | | 2/2005 |
| WO | 2009/092807 | | 7/2009 |
| WO | 2009/125582 | | 10/2009 |

OTHER PUBLICATIONS

JP Office Action dated Feb. 4, 2014, with English translation; Application No. 2012-507825.

Translation of the Second Chinese Office Action, dated Aug. 28, 2013, from corresponding CN application.

* cited by examiner

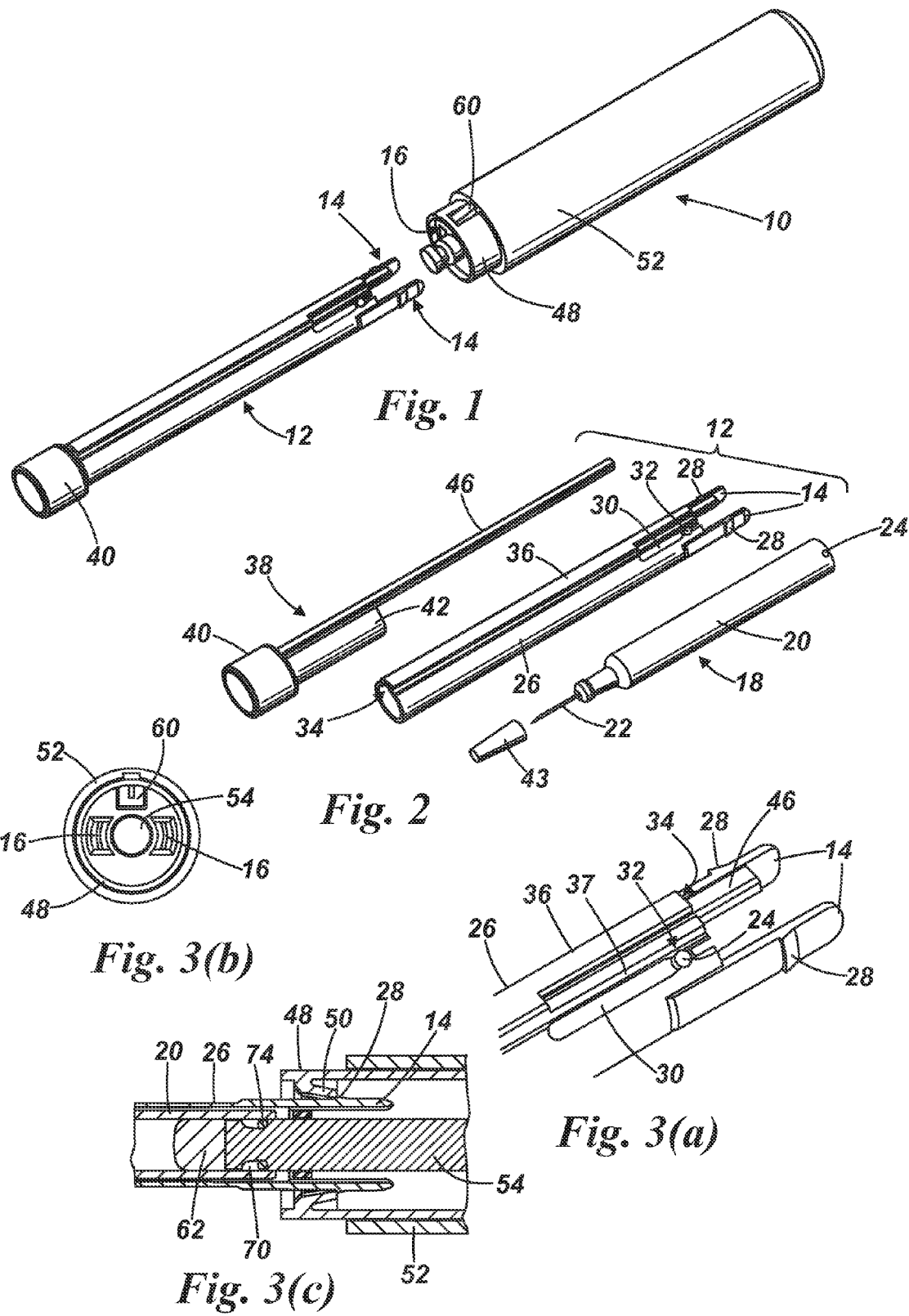

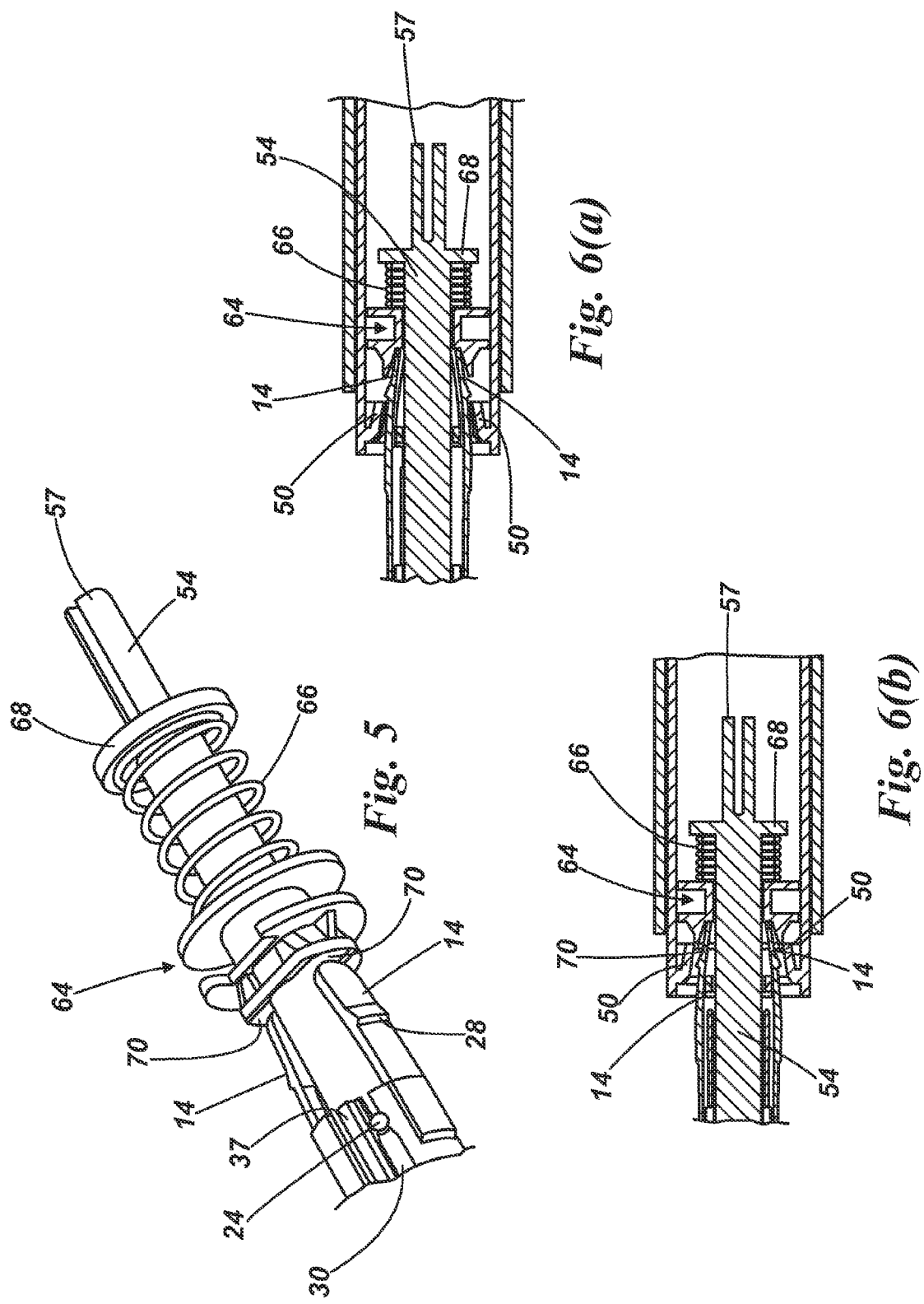

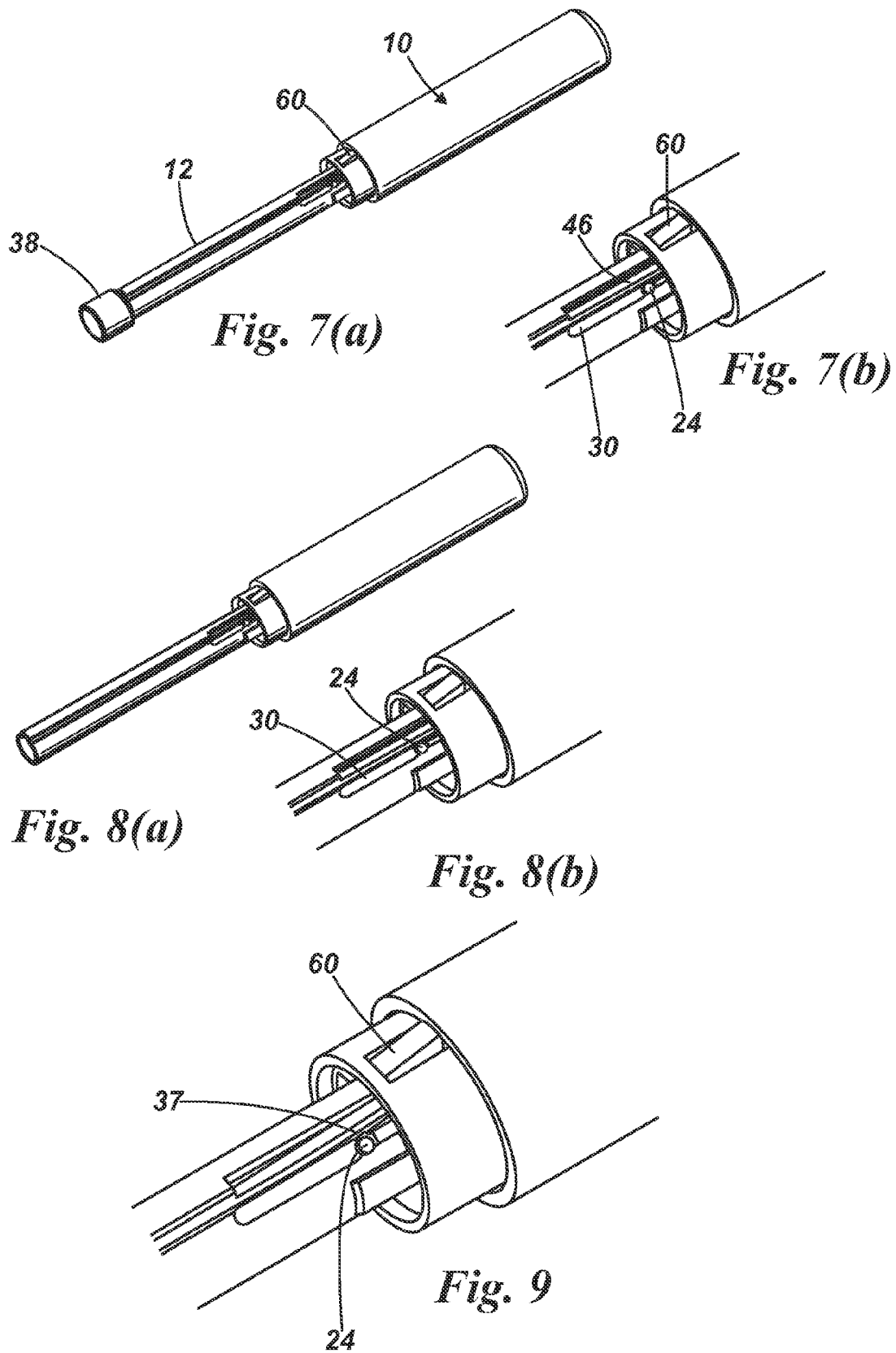

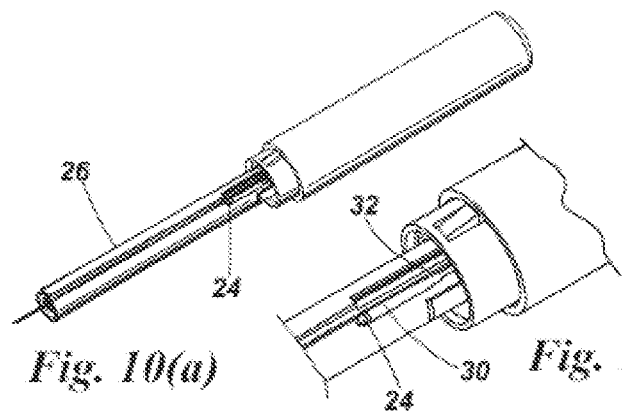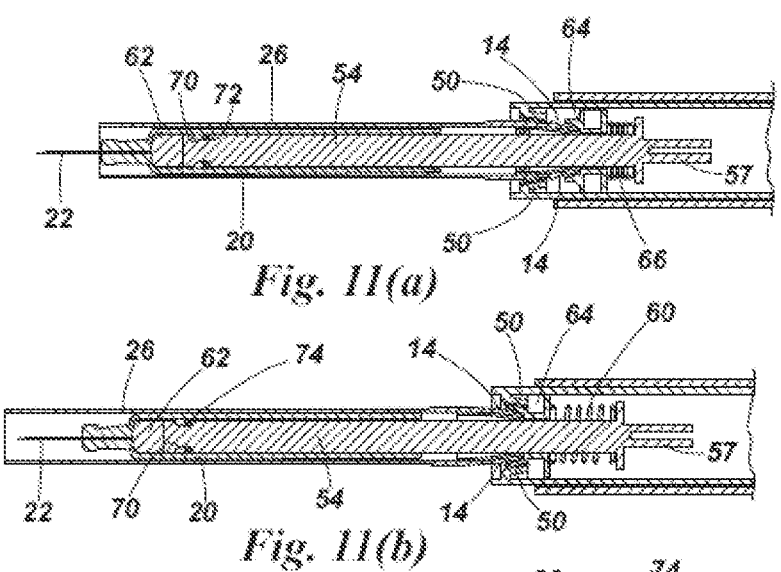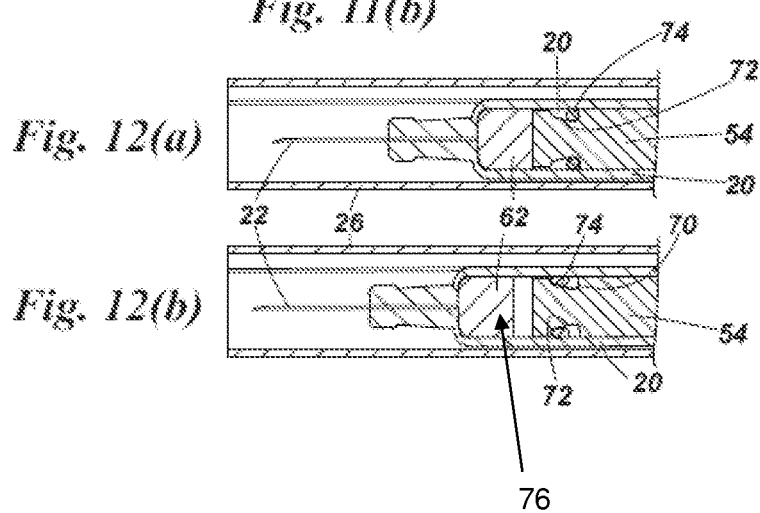

INJECTION DEVICES

BACKGROUND OF THE INVENTION

1. Field of the Invention

This invention relates to injection devices and, in particular, but not exclusively, to autoinjection devices.

2. Description of the Related Art

Many autoinjection devices are single use, disposable devices. With the growing awareness of the environmental impact of such devices once used, there is a desire to make part of such devices reuseable and to reduce the proportion of the device that is single use and disposable. Furthermore, it is desirable to design the disposable, single use, part of the device so that it is readily adapted for recycling.

BRIEF SUMMARY OF THE INVENTION

Accordingly, in one aspect, this invention provides a syringe assembly comprising:
- a syringe having a body and a needle, and
- a shield slideably mounted around said syringe for telescopic movement between a retracted position in which the syringe needle is exposed in use and an extended position in which the needle is at least partially shrouded by said shield,
- wherein said syringe body has a feature thereon which cooperates with an associated feature on the shield to control relative movement thereof.

Advantageously said syringe body and said feature are of moulded plastics material. Preferably said cooperating features limit the extent of telescopic movement of the syringe and the shield, and further may be operable releasably to latch said shield in a forward position relative to the syringe.

The cooperating features may typically comprise a projection on one of the syringe or shield, cooperating with a control slot on the other thereof. The slot may be provided at one end region with a latch recess for releasably retaining said projection, and the wall of the slot, at least in the region of said latch recess, is preferably resiliently deformable to allow said projection to snap out of said recess to allow said shield to move rearwardly relative to the syringe. There may be a locking member engageable adjacent or near said slot for inhibiting resilient movement of said latch recess to prevent release of said projection, and the locking member may be engageable by being longitudinally slideable into a locking slot provided alongside said control slot. The locking member may carry at its forward end a cap for closing the forward end of said shield, when applied to the forward end of said shield, and with the locking member slid longitudinally into said locking slot. Where as is common the syringe includes a boot covering said needle prior to use, the cap conveniently includes means for engaging said boot when said cap is applied to said shield, such that removal of said cap removes said boot.

Where said syringe assembly is adapted to be releasably coupled in use to the drive assembly of an autoinjection device in which the drive assembly includes a drive for expelling a dose from the syringe, a trigger for releasing said drive, and a safety arrangement for preventing inadvertent actuation of said drive, said locking member is preferably arranged to release said safety arrangement and/or unlock said safety arrangement for subsequent release, when said locking member is removed from said shield.

A number of different configurations are possible, but the syringe may typically be carried inside said shield by direct sliding engagement therebetween.

In order to reduce the number of parts and amount of material that is required to be disposed of in a multi-use autoinjector arrangement, of the type in which a syringe assembly as described is adapted to be releasably coupled in use to the drive assembly of the autoinjector device, the syringe assembly is preferably coupled to said drive assembly in use by interengagement of a portion of said shield with said drive assembly, so that the shield acts as both shield and container, thereby obviating the need for a separate container so that just the syringe and the shield are disposed of post use. The shield may include one or more features for snap engagement in use with an associated one or more features on said drive assembly. To automate ejection the syringe and shield after use, said drive may be adapted to uncouple said shield from said drive assembly on approaching or reaching the forwardmost extent of movement.

The invention extends to an autoinjection device including a removable syringe as set out above.

In order to provide simple, safe and reliable operation, and thereby a device whose use is intuitive yet inherently safe, the inventors have designed an autoinjection device in which a number of locks keep the device in a safe condition prior to use, but are all released by removal of a single element.

Accordingly, in another aspect of this invention provides an autoinjection device comprising:
- a syringe having a needle which prior to injection carries a boot;
- a shield movable relative to said syringe between an extended position in which the needle is at least partially shrouded and a retracted position in which the needle is exposed;
- a drive assembly for expelling a dose from the syringe;
- a trigger for actuating said drive assembly;
- a safety arrangement for preventing inadvertent actuation of said drive assembly, and
- a boot remover applied to the forward end of said autoinjector and adapted to engage said boot, said boot remover being arranged to prevent movement of said syringe relative to said shield in at least one direction, and to prevent release of said safety arrangement until said boot remover is removed from the front end of the device.

Conventional autoinjector devices are either single use disposable items or, where multi-use, require the user to open the device to remove and insert the syringe or cartridge. This latter carries the risk of exposure to potential needle stick injury and also requires manual dexterity of the user. The inventors have therefore designed an autoinjector where on completion of the injection, the syringe assembly is automatically released from the autoinjector body.

Accordingly, in another aspect, this invention provides an autoinjection device comprising:
- a drive assembly and a syringe assembly adapted to be coupled and uncoupled in use, the syringe assembly including a shield and a syringe movable with respect to said shield and having a needle, the drive assembly including a drive and a trigger for actuating said drive to drive a plunger forwardly to move the syringe forwardly relative to the shield and to expel a dose from the syringe, characterised in that the syringe assembly is coupled to said drive assembly by one or more engagement elements on said shield engaging one or more directly or indirectly cooperating elements on said drive assembly, and in that said plunger or a part associated therewith disengages said features as it approaches or reaches its forward position, to release the syringe assembly.

The action of releasing the syringe assembly also provides an important confirmation to the user that injection is complete.

In a number of applications, it may be desirable to resist or obstruct movement of a syringe plunger in the separation direction, for example to prevent re-use or to hold the syringe on the plunger whilst a shield is deployed post-injection.

Accordingly, in another aspect, this invention provides an injection device comprising:
- a syringe having a body and a plunger having a portion extending within the body of said syringe and adapted to expel a dose, including means to impart significantly greater resistance to separating movement of the plunger and the syringe, than in the opposite direction.

As set out above, there is a growing desire to reduce the amount of material that has to be disposed of post-injection.

Accordingly, in yet another aspect, this invention provides an autoinjection device comprising:
- a reusable drive assembly releasably coupled to a disposable syringe assembly, the syringe assembly comprising a shield and a syringe, the syringe having a needle, the syringe being telescopically movable within said shield, between a retracted position in which the need is at least partially shielded, and an extended position in which the needle is exposed, the drive assembly comprising a drive and a trigger for actuating said drive arrangement to expel a dose from the syringe, characterised in that the syringe assembly is releasably coupled to the drive assembly by engagement of a coupling portion on the shield with a coupling portion in the drive assembly.

Whilst the invention has been described above, it extends to any inventive combination of the features set out above or in the following description or claims.

BRIEF DESCRIPTION OF THE DRAWINGS

The invention may be performed in various ways and, by way of example only, an embodiment thereof will now be described with reference to the following drawings, in which:

FIG. 1 is a general view of an embodiment of autoinjection device, showing the reuseable drive assembly and the disposable syringe assembly prior to coupling;

FIG. 2 is a general view of the components making up the syringe assembly;

FIGS. 3(a) to (c) are detailed views showing the coupling engagement between the syringe assembly and the drive assembly;

FIG. 5 is a detailed view on the mechanism associated with the plunger for releasing the syringe assembly from the drive assembly at the end of the forward stroke of movement of the plunger;

FIGS. 6(a) and (b) are longitudinal section views through a forward part of the drive assembly showing operation of the release mechanism;

FIGS. 7(a) and (b) are a view of the syringe assembly coupled to the drive assembly prior to removal of the boot remover, and a detailed view on the syringe latch respectively;

FIGS. 8(a) and (b) are views similar to FIGS. 5(a) and (b) but after removal of the boot remover;

FIG. 9 is a detailed view on the syringe latch showing resilient flexing thereof to release the shield latch pip on the syringe;

FIGS. 10(a) and (b) are views similar to FIGS. 6(a) and (b) but following release of the plunger to drive the syringe forwardly to expose its needle;

FIGS. 11(a) and (b) are longitudinal section views through the syringe assembly showing the release mechanism that re-extends the shield over the syringe to shield the needle on completion of the injection and release of the syringe assembly, and FIGS. 12(a) and (b) are longitudinal sections through the forward end of the syringe assembly showing operation of the one way gripper arrangement between the syringe plunger and the syringe body 20.

DETAILED DESCRIPTION OF THE PREFERRED EMBODIMENTS

Figure 4:
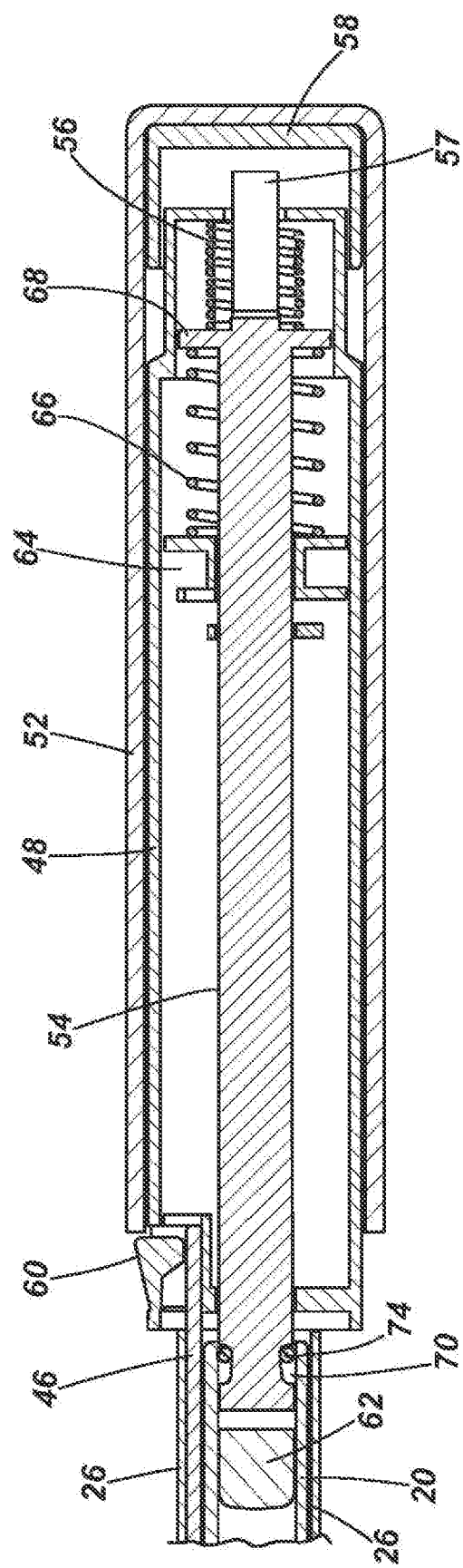
FIG. 4 is a longitudinal cross-section view through the drive assembly, with the safety catch locked.

Referring initially to FIG. 1, the illustrated embodiment of autoinjection device comprises a drive assembly 10 releasably coupled to a syringe assembly 12 by a pair of coupling tongues 14 on the syringe assembly designed to snap fit into locking recesses 16 on the drive assembly, as to be described below in relation to FIGS. 3(a) to (c). The drive assembly is designed to be reusable whereas the syringe assembly is a single use disposable item. In order to reduce the environmental impact, the syringe assembly is made of just three components as illustrated in FIG. 2, all of which, with the exception of the syringe needle, are moulded from recyclable plastics material.

As seen in FIG. 2, the syringe assembly comprises a moulded plastic syringe 18 having a cylindrical body 20 from the forward end of which extends a needle 22 and provided at its rear end with a radially projecting shield latch pip 24. The needle shield 26 is of open ended shell form with the coupling tongues 14 extending rearwardly therefrom. The coupling tongues 14 have coupling ramps 28 which effect a snap fit coupling as to be described below and are capable of resilient flexing movement. At the rear end of the needle shield 26 (and viewable on enlarged scale in FIG. 3(a)) is a control slot 30 designed slideably to receive the shield latch pip 24. At its rear end, the control slot 30 has a latch recess 32 in which the shield latch pip 24 can be releasably latched. A locking slot 34 runs in a keyway 36 extending along the length of the needle shield 26 with the keyway 36 being cut away at its rear end to leave a resilient finger 37 defining one edge of the slot 30 and allowing resilient flexing to release the latch recess 32 when the locking slot 34 is empty.

A boot remover 38 carries at its forward end a cap 40 from the rear of which extends a cylindrical boot remover portion 42, having internal barbs or other suitable grip elements (not shown) to engage a boot 43 which covers the needle 22 prior to use. Extending rearwardly from the cap 40 is a boot remover finger 46 designed to be a slideable fit in the locking slot 34. When the boot remover 38 is fitted to the front end of the shield (as seen for example in FIGS. 1 and 3(a)) the boot remover finger 46 extends alongside the slot 30 to protrude rearwardly from the edge of the needle shield 26 to lock a safety catch arrangement as to be described below.

Referring now to FIGS. 3(a) to (c), the syringe assembly is coupled to the drive assembly by offering up the tongues 14 to the locking recesses 16 and pushing the syringe assembly rearwardly to effect a snap fit. The main body portion 48 of the drive assembly 10 has a tooth 50 extending rearwardly and inwardly from each locking recess 16 and designed so that when the coupling tongues 14 pass through the recesses 16, the ramps 28 snap fit behind the teeth 50 to lock the syringe assembly 12 against forward movement.

Referring now to FIG. 4, the drive assembly 10 includes a trigger sleeve 52 slideably mounted around the outside of the main body 48. A plunger 54 is slideably mounted within the main body 48 and urged forwardly by a main drive spring 56. The plunger has at its rear end a split arrowhead locking latch 57 or similar which holds the plunger in a rearward position in the main body with the drive spring energised. A trigger cap 58 is slideably mounted on the rear end of the main body 48 and movable forwardly from a rest position to squeeze together the split arrowhead to release the locking latch 57 and to release the plunger 54 for forward movement. At the forward end of the main body 48 there is a flexible safety catch 60 which, when in the 'safe' position shown in FIG. 4, prevents forward movement of the trigger sleeve 52 to the firing position. The safety catch 60 is held in its 'safe' position in FIG. 4 by the rearward end of the boot remover finger 46. Upon forward withdrawal of the boot remover finger 46, this constraint is removed thereby unlocking the safety catch so that it can be cammed or pushed manually down as the trigger sleeve 52 is moved to a forward position in which it moves the trigger cap 58 to release the plunger. As evident from FIG. 4, upon forward movement, the plunger 54 will engage at its forward end the syringe bung 62.

Referring now more particularly to FIGS. 5 and 6(a) and (b), a release collar 64 is slideably mounted towards the rear end of the plunger and biased forwardly by an ejection spring 66 acting between a flange 68 integral with the plunger and the rear end of the release collar 64. The release collar 64 has at its forward end opposed part-conical release surfaces 70 designed to urge the coupling tongues 14 inwards to release the coupling ramps 28 to uncouple the syringe assembly 12 from the drive assembly 10 at the end of an injection. As seen in FIG. 6(a), as the plunger approaches its forwardmost position, the release collar 64 squeezes the coupling tongues 14 inwards and then pushes the shield 26 forwardly relative to the drive assembly as seen in FIG. 6(b).

In use, the drive assembly is loaded if necessary by pushing the plunger 54 back into the main body so that the plunger is latched in its rearward position and the trigger sleeve is locked in a rearward position by the safety catch 60. A fresh syringe assembly 12 with its boot remover 38 closing the forward end and with the syringe latched in its rearward position relative to the shield 26 is offered up to the drive assembly 10 and snap fitted into position with the tongues 14 locked into the locking recesses 16. In this configuration, the boot remover 38 fulfils several different functions. It closes off the front end of the shield; the boot remover finger 46 prevents resilient flexing movement of the resilient finger 37 and thus prevents unlatching and forward movement of the syringe relative to the shield; the boot remover finger 46 also prevents release of the safety catch 60, as seen in FIGS. 7(a) and (b).

Removal of the boot remover removes the boot 43 from the syringe needle 22 and unlocks the resilient finger 37 so that the syringe is ready for forward movement. Finally, the safety catch 60 is unlocked. The assembled autoinjector is then offered up to the injection site with the front end of the shield placed against the skin. The safety catch 60 is released and the trigger sleeve 52 moved forwardly to release the plunger. Upon initial release of the plunger, it acts via the piston bung 62 and the liquid charge in the syringe which acts initially as a solid to move the syringe 18 bodily forward so that the shield latch pip 24 springs out of the latch recess 32 and moves down the control slot 30 to the position shown in FIGS. 10(a) and (b) with its needle 22 extended. The syringe is then prevented from further movement by the pip reaching the forward end of the slot and so the plunger now moves the bung 62 forwardly to express the dose.

As shown in FIGS. 11(a) and (b), as the plunger 54 reaches its forward end, the release collar 64 squeezes the ends of the coupling tongues 14 together to uncouple the shield 26 from the main body of the drive assembly. At this point the shield 26 does not yet move forwardly relative to the syringe because the injection device is still pressing against the skin. On release of that pressure, the needle shield 26 moves forwardly under the influence of the ejection spring 66 until the shield latch pip 24 snaps back into the latch recess 33.

During this movement, it is important that the syringe does not move forwardly with the shield. For this purpose, as shown in FIGS. 12(a) and (b) there is a one-way clutch arrangement provided between the plunger and the syringe body 20. The plunger has an annular groove 70 with a ramped or frusto conical base 72, which receives a 'O' ring 74. When the plunger is moving towards or into the bore 76 of the syringe the 'O' ring 74 is urged towards the deeper part of the groove 70 thus providing little or no resistance to movement, as shown in FIG. 12(a). However, movement of the plunger in the opposite sense drives the 'O' ring into engagement with the syringe body 20 thus tending to resist rearward movement, as shown in FIG. 12(b). The resistance to rearward movement of the plunger is designed to be sufficient to hold the syringe against forward movement to ensure proper extension and latching of the needle shield, but to be overcome when it is required to slide the uncoupled syringe assembly off the extended plunger.

The boot remover 38 is reapplied to the shield with the boot remover finger 46 sliding along the slot 34 to block resilient movement of the resilient finger 37. The syringe assembly 10 is now safe for disposal. Apart from the needle which will typically be of metal material, the remainder of the syringe assembly may be made principally or wholly of recyclable plastics material such as thermoplastic material.

The invention claimed is:

1. A syringe assembly comprising:
   a syringe having a syringe body and a needle extending from a distal-most application end of the syringe body; and
   a shield slideably mounted around the syringe body for telescopic movement between a retracted position in which the syringe needle is exposed in use and an extended position in which the needle is at least partially shrouded by the shield,
   wherein the shield is provided with a longitudinal control slot extending in a longitudinal direction along the shield, and the syringe body is provided with a projection which cooperates with the longitudinal control slot on the shield to control relative longitudinal movement of the syringe along the shield,
   wherein the projection slideably engages the slot to control the relative longitudinal movement of the syringe along the shield,
   wherein the control slot is provided with a latch recess configured to releasably retain the projection,
   wherein the wall of the slot, at least in the region of the latch recess, is resiliently deformable to allow the projection to snap out of the latch recess to allow the shield to move rearwardly relative to the syringe, and
   the syringe assembly further comprises a locking member engageable adjacent or near the control slot to inhibit resilient movement of the latch recess to prevent release of the projection.

2. The syringe assembly according to claim 1, wherein the syringe assembly is configured to be releasably coupled in use to the drive assembly of an autoinjector device, the drive assembly including a drive adapted in use to express a dose from the syringe, and wherein the syringe assembly is coupled to the drive assembly in use by interengagement of a portion of the shield with the drive assembly.

3. The syringe assembly according to claim 2, wherein the shield includes one or more features for snap engagement in use with an associated one or more features on the drive assembly.

4. The syringe assembly according to claim 2, wherein, in use, the drive is adapted to uncouple the shield from the drive assembly on approaching or reaching the forwardmost extent of movement.

5. The syringe assembly according to claim 1, wherein the locking member carries at its forward end a cap configured to close the forward end of the shield, when applied to the forward end of the shield, and with the locking member slid longitudinally into the locking slot.

6. The syringe assembly according to claim 5, wherein the syringe includes a boot covering the needle prior to use, and the cap includes means for engaging said boot when the cap is applied to the shield, such that removal of the cap removes the boot.

7. An autoinjection device comprising:
a syringe assembly as claimed in claim 1, the needle carrying a boot prior to injection;
a drive assembly configured to expel a dose from the syringe, the drive assembly including
a drive,
a trigger configured to actuate the drive assembly, and
a safety arrangement configured to prevent inadvertent actuation of the drive assembly in a locked position; and
a boot remover applied to the forward end of the autoinjector and adapted to engage the boot, the boot remover being configured to
(i) prevent movement of the syringe relative to the shield in at least one direction, and
(ii) prevent release of the safety arrangement of the drive assembly when the boot is in place on the needle,
wherein removal of the boot remover from a distal application end of the autoinjection device enables the safety arrangement of the drive assembly to be unlocked to allow actuation of the drive assembly.

8. The autoinjection device according to claim 7, wherein the boot remover includes a boot removal finger.

9. The syringe assembly according to claim 1, wherein the syringe body and the longitudinal slot are made of molded plastics material.

10. The syringe assembly according to claim 1, wherein the longitudinal slot and the projection cooperate to limit the extent of telescopic movement of the syringe and the shield.

11. The syringe assembly according to claim 1, wherein the longitudinal slot and the projection are operable releasably to latch the shield in a forward position relative to the syringe.

12. The syringe assembly according to claim 1, wherein said locking member is engageable by being longitudinally slideable into a locking slot provided alongside said control slot.

13. The syringe assembly according to claim 1, wherein the syringe assembly is adapted to be releasably coupled in use to a drive assembly of an autoinjection device, the drive assembly including a drive configured to expel a dose from the syringe, a trigger configured to release the drive, and a safety arrangement configured to prevent inadvertent actuation of the drive, and wherein the locking member releases the safety arrangement and/or unlocks the safety arrangement for subsequent release, when the locking member is removed from the shield.

14. The syringe assembly according to claim 1, wherein the syringe is carried inside the shield by direct sliding engagement therebetween.

15. An autoinjection device comprising a removable syringe assembly according to claim 1.

* * * * *